United States Patent [19]

Allen

[11] Patent Number: 5,147,956
[45] Date of Patent: Sep. 15, 1992

[54] ABSORBENT PRODUCTS AND THEIR MANUFACTURE

[75] Inventor: Adrian S. Allen, North Yorkshire, England

[73] Assignee: Allied Colloids Ltd., England

[21] Appl. No.: 521,336

[22] Filed: May 9, 1990

Related U.S. Application Data

[63] Continuation-in-part of Ser. No. 123,572, Nov. 20, 1987, Pat. No. 4,992,172.

[30] Foreign Application Priority Data

May 10, 1989 [GB] United Kingdom ............... 8910788

[51] Int. Cl.$^5$ .......................................... C08F 220/26
[52] U.S. Cl. ............................ 526/318.42; 576/318.5; 576/333; 524/833; 524/916
[58] Field of Search .................. 526/318.5, 318.42; 524/833, 916; 523/111

[56] References Cited

U.S. PATENT DOCUMENTS

| | | | |
|---|---|---|---|
| Re. 30,029 | 6/1979 | Smith | 128/285 |
| 3,311,583 | 3/1967 | Bearden | 526/318.42 |
| 3,719,647 | 3/1973 | Hardy | 260/86.1 R |
| 3,884,964 | 5/1975 | Otrhalek et al. | 560/205 |
| 3,926,891 | 12/1975 | Gross et al. | 523/412 |
| 3,980,663 | 9/1976 | Gross | 524/389 |
| 3,995,998 | 12/1976 | Rowland | 8/115.6 |
| 4,041,121 | 8/1977 | Smith | 264/191 |
| 4,057,521 | 11/1977 | Gross | 524/379 |
| 4,066,584 | 1/1978 | Allen et al. | 523/111 |
| 4,104,214 | 8/1978 | Meierhoefer | 523/105 |
| 4,351,922 | 9/1982 | Yoshida | 526/116 |
| 4,413,769 | 2/1984 | Yoshida | 524/555 |
| 4,524,186 | 6/1985 | Nagase | 525/328.8 |
| 4,725,655 | 2/1988 | Denzinger | 526/65 |
| 4,764,554 | 8/1988 | Tonge | 524/558 |
| 4,800,220 | 1/1989 | Ribba | 526/238.23 |
| 4,962,172 | 10/1990 | Allen | 526/318.42 |

FOREIGN PATENT DOCUMENTS

| | | |
|---|---|---|
| 0213799 | 3/1987 | European Pat. Off. . |
| 0268498 | 5/1988 | European Pat. Off. . |
| 2546392 | 4/1976 | Fed. Rep. of Germany . |
| 7719027 | 1/1978 | France . |
| 473734 | 2/1972 | Japan . |
| 5884819 | 5/1983 | Japan . |
| 62-69898 | 3/1987 | Japan . |
| 783755 | 9/1957 | United Kingdom . |
| 0940766 | 11/1963 | United Kingdom . |

OTHER PUBLICATIONS

Chemical Abstracts, vol. 96, No. 20, May 1982, p. 35, abstract No. 163649q, Columbus, Ohio, US; and JP-A-81 161 413 (Kao Soap Co., Ltd.) Nov. 12, 1981.
Patent Abstracts of Japan, vol. 6, No. 19 (C-90) [897], Feb. 3, 1982; and JP-A-56 141 308 (Nippon Hatsujiyou K.K.) May 11, 1981.

*Primary Examiner*—Joseph L. Schofer
*Assistant Examiner*—M. Nagumo
*Attorney, Agent, or Firm*—Ostrolenk, Faber, Gerb, Soffen

[57] ABSTRACT

A water soluble, substantially linear, polymer is made by copolymerization of a water soluble blend of monoethylenically unsaturated monomers comprising carboxylic acid monomers such as acrylic acid and a hydroxylic monomer of the formula $CHR^1=CR^2-Y-M_a-H$ where $R^1$ is hydrogen or carboxy, $R^2$ is hydrogen, carboxy or methyl, Y is O, $CH_2O$ or COO, M is alkyleneoxy and a is at least 5. This polymer can be cross linked, generally after being shaped by extrusion or other shaping of an aqueous solution of the polymer, to form cross linkages between the carboxyl and hydroxyl groups. The shaped elements can have water absorbency and can be in the form of, for instance, fibers or films.

14 Claims, No Drawings

ABSORBENT PRODUCTS AND THEIR MANUFACTURE

This is a continuation-in-part of application Ser. No. 07/123,572, filed Nov. 20, 1987 and now U.S. Pat. No. 4,992,172.

This invention relates to water absorbent, water insoluble polymers elements made by forming a substantially linear polymer and then reacting pendant groups in the polymer while it is in the shape of the desired element so as to form cross linkages.

This general process is known for the manufacture of cross linked beads, for instance in a process comprising forming beads of a linear polymer by reverse phase bead polymerisation followed by heating the beads to effect cross linking. Such a process is described at, for instance Chemical Abstracts 96:163649q. However the process is of particular value when applied to the production of shaped polymeric elements made by shaping a solution of the linear polymer and then cross linking it.

In U.S. Pat. No. 4,057,521 it was proposed that the linear polymer should be a copolymer of acrylic acid and N-methylol acrylamide, with the intention that cross linking would occur as a result of reaction between the methylol and carboxylic pendant groups. In EP 0268498 (U.S. Ser. No. 123,572 filed 20th Nov. 1987 and now U.S. Pat. No. 4,962,172) the linear polymer was formed from a monomer that provides carboxylic acid monomer groups and a monomer that provides hydroxyl groups and that can react with the carboxylic acid groups to form ester cross linkages that contain only carbon and oxygen atoms in the linkages.

A wide range of classes of hydroxyl-containing monomers were mentioned and specific named monomers were hydroxy ethyl (meth) acrylate, hydroxy propyl (meth) acrylate, di- or tri- alkylene glycol mono (meth) acrylate where alkylene is ethylene or propylene and glyceryl mono (meth) acrylate. Hydroxy ethyl methacrylate, tripropylene glycol monoacrylate and glyceryl monoacrylate were each used in an example but the majority of the examples and working data in the specification related to hydroxy propyl methacrylate as the hydroxyl-containing monomer to be condensed with the carboxyl groups of acrylic acid.

In practice, tripropylene glycol monoacrylate suffers from the disadvantage that commercially it is always contaminated with tripropylene glycol diacrylate, with the result that the extent of cross linking is unpredictable.

Although hydroxy propyl (meth) acrylate frequently gives a product that has satisfactory absorption characteristics, the results can be rather variable and it would be desirable to be able to obtain higher absorption characteristics more reproducibly.

I have now surprisingly found that it is possible to achieve this if the hydroxyl-containing monomer is based on a polyalkylene glycol containing at least 5 oxyalkylene groups.

A water soluble substantially linear polymer according to the invention is formed by copolymerisation of a water soluble blend of monoethylenically unsaturated monomers comprising carboxylic monomer that provides carboxylic groups and hydroxylate monomer that provides hydroxyl groups and that has the formula $CHR^1=CR^2-Y-M_a-H$ where $R^1$ is hydrogen or carboxy, $R^2$ is hydrogen, carboxy or methyl, Y is O, $CH_2O$ or COO, M is alkyleneoxy and a is at least 5, and the linear polymer is capable of being cross linked by esterification of the said carboxyl groups with the said hydroxyl groups.

A water absorbent, water insoluble polymer according to the invention is formed from this substantially linear polymer by esterification of the carboxyl and hydroxyl groups to form cross linkages of the formula $-Y-M_1-OCO-$, where Y, M and a are as defined above. The absorbent polymer is highly absorbent and generally has a gel capacity of at least 50 grams deionized water per gram dry polymer.

Since the polymer is water insoluble and water absorbent, it will be present in the form of shaped elements such as particles, films, fibres, or coatings. The linear polymer can be formed by polymerisation in the shape of the desired elements, for instance by reverse phase bead polymerisation to make beads in the general manner described in Chemical Abstracts 96:163649q, and the linear polymer is then caused to undergo esterification to form the desired cross links.

Preferably however the linear polymer is formed and is then shaped into the shape of the desired elements, and is then subjected to the esterification.

The shaped elements, especially those formed by shaping the linear polymer and then effecting the esterification, the methods of producing the shaped elements, and solutions of the linear polymer form further parts of the invention.

By the invention it is possible to achieve higher and more reproducible absorption characteristics in the final absorbent polymers than were possible in the polymers described in EP 268498. Although I do not wish to be bound by theory, I think that the extent of cross linking in EP 268498 was rather variable because it was difficult for the hydroxyl groups reliably to react with carboxyl groups in adjacent polymer chains. Thus the amount of hydroxyl groups was low and their chain length was short. There was therefore a significant risk that a hydroxyl group in one chain would not be in the correct steric position to esterify with the carboxylic group in another chain and it would, instead, either remain unreacted or esterify with the carboxylic group in the same chain. By providing a much longer linkage between the chain and the hydroxylic group it seems that I probably improve signicantly the statistical chances of the hydroxyl group locating and esterifying with a carboxyl group of another polymer chain.

If this theory is right, it might have been observable to a small extent in example 4 of EP 268498, when using tripropylene glycol monoacrylate. However this material is, as mentioned above, commercially always contaminated with tripropylene glycol diacrylate and so the material that was used would have contained diethylenically unsaturated monomer and this would have interfered with the formation of the desired linear polymer, possibly resulting in cross linking at that stage. In the invention, it is necessary that the blend of ethylenically unsaturated monomer should consist essentially only of monoethylenically unsaturated monomer, and in particular that it should not be contaminated by accidental or deliberate incorporation of di- or poly- ethylenically unsaturated monomer.

When Y is oxygen the hydroxyl-containing monomer can be regarded as a derivative of a vinyl alcohol and when Y is $CH_2O$ the monomer can be regarded as a derivative of an allyl alcohol. Preferably however Y is COO in which event the monomer can be regarded as an acrylate. The monomer may be a hydroxy polyoxy alkylene ester of, for instance, itaconic acid, fumaric acid, maleic acid, methacrylic acid, crotonic acid or, preferably, acrylic acid. Preferably $R^1$ is hydrogen and $R^2$ is methyl or, most preferably, hydrogen.

The groups M can be selected from propyleneoxy, ethyleneoxy, butyleneoxy or other suitable alkyleneoxy groups, but preferably some or all of them are propyleneoxy. If mixed alkyleneoxy groups are present then they may be distributed randomly or in blocks along the alkyleneoxy chain. The alkyleneoxy chain preferably contains at least 6 alkyleneoxy groups and a can be up to 100 or even 200 but often there is no advantage in having more than 10, or at the most 20, alkyleneoxy groups in the chain.

It is particularly preferred that the alkyleneoxy chain contains at least 6 propyleneoxy groups, for instance being based on hexapropylene glycol.

The hydroxylic monomer can be a commercially available material or can be synthesised in known manner, for instance by polycondensing alkylene oxide on to acrylic acid or other monomer of the formula $CHR^1=CR^2-YH$. If the monomer is made by condensing a preformed polyalkylene glycol onto the monomer $CHR^1=CR^2-YH$ then it is preferred that one of the hydroxy end groups of the polyalkylene glycol should be blocked before the reaction, e.g., by methyl, so as to minimise the formation of di-unsaturated monomer. The blocking group should then generally be removed before the internal esterification reaction and generally it is removed before the formation of the linear polymer, and generally before the monomer is introduced into the water soluble blend of monomers.

However the invention does, of course, also include polymers formed by internal esterification between the carboxyl and hydroxyl groups when either or both of them are blocked by a group that is removed during the esterification, provided that the blocking group (for instance a methyl ester group on the carboxylic or a methyl ether group on the hydroxyl) does not prevent the internal esterification reaction occurring.

Suitable carboxylic monomers are (meth) acrylic acid or any of the other conventional ethylenically unsaturated carboxylic acids, optionally with 2-acrylamido-2-methyl propane sulphonic acid or any of the other conventional ethylenically unsaturated sulphonic acids, or allyl sulphonate. Carboxylic and sulphonic monomers may be present in the final polymer in free acid or water soluble salt form, suitable salts being formed with ammonia, amine or alkali metal. The proportion of salt and free acid groups can be adjusted after formation of the cross linked polymer or after polymerisation of the linear polymer or before polymerisation. Generally the ratio of free carboxylic acid/alkali metal or other salt carboxylic acid groups in the final polymer (and often also in the monomers that are used to form the linear polymer) from 1:1 to 1:10. The ratio is usually at least 1:2 and often 1:3. It is generally below 1:6 and often below 1:5.

In many instances it is desirable, in order to promote the internal cross linking reaction, that at least some of the carboxylic acid groups should be present as free acid groups before the cross linking occurs. For instance, for this purpose, it may be adequate for 10 to 75%, preferably 25 to 75%, of the acid groups to be in free acid form before the cross linking occurs.

The amount of hydroxyl monomer is preferably 0.1 to 15%, generally 1 to 10%, and the amount of carboxylic acid (or salt) is preferably above 50%, and often above 70%. These amounts are by weight based on total monomers. Often the blend is formed of 90-99% acrylic acid (some being in salt form) and 1 to 10% of the hydroxyl monomer where $R^1$ is H, $R^2$ is H or $CH_3$ and Y is COO.

Polymers formed solely from the defined carboxylic acid (as free acid and/or salt) and hydroxyl monomers tend to be rather brittle and it is preferred to include in the polymer plasticising monomers. The use of hydroxy alkyl esters containing 6 to 10 carbon atoms will promote plasticisation but it is generally desirable to include additional plasticising monomer so as to promote plasticisation and improve flexibility of the resultant polymer. The monomers may be aromatic ethylenically unsaturated monomers, such as acrylonitrile or styrenes (e.g., styrene or substituted styrenes), but they are preferably alkyl esters of (meth) acrylic acid or other suitable unsaturated carboxylic acid. Vinyl acetate and other vinyl esters may be used. The alkyl group of the ester generally contains less than 24 carbon atoms and usually 2 or more. Preferred alkyl groups contain 1 to 10 carbon atoms, especially ethyl and also higher alkyl groups such as 2-ethyl hexyl or other C6-C10 alkyl groups. Particularly preferred plasticising monomers are methyl or ethyl (meth) acrylate, butyl (meth) acrylate and 2-ethyl hexyl (meth) acrylate. The amount is generally 0 to 45% by weight, and is generally at least 2% and often at least 10%. The amount is usually 10 to 30% by weight based on the monomers used for forming the substantially linear polymer.

Other non-ionic monomers that may be used include ethylenically unsaturated monomers that carry a pendant polyalkyleneoxy chain that is terminated by a hydrophobic group containing at least 8 carbon atoms, for instance as described in EP 213799. The use of such monomers, typically in amounts of 1 to 50%, generally 5 to 30%, by weight in the total monomer blend can give improved plasticisation, absorptive capacity and non-tackiness, especially in aqueous electrolytes.

After forming the solution of polymer, it can then be shaped and then caused to undergo the internal esterification. Shaping can be by any of the methods described in EP 268498 and thus can be by impregnating or coating the solution on to a film or fibrous core, such as a woven or non-woven sheet or a yarn, filament or film, by using the solution as a laminating material for laminating an absorbent substrate to a sheet substrate or by foaming the solution. Preferably however the shaping is by extrusion to provide a shaped element that has one dimension at least five times a second dimension. Thus films and fibres can be made.

The substantially linear, water soluble, polymer may be formed from the monomer blend in any conventional manner. It may be pre-formed and then dissolved to form a polymer solution. For instance it may be made by reverse phase polymerisation if the monomer blend is soluble in water or by water-in-oil emulsion polymerisation if the blend is insoluble in the water, e.g., at a low pH. However this can incur the risk that the polymer may be contaminated by surfactant and this is undesirable. Preferably therefore the polymer is made by aqueous solution or other solution polymerisation methods. It may have been dried, but is preferably not. Generally it is formed as a bulk solution by solution polymerisation in the solvent in which it is to be shaped (generally water).

The polymerisation can be conducted in conventional manner in the presence of conventional initiators and/or chain transfer agents to give the desired molecular weight. If the molecular weight of the linear polymer is too low, the physical properties of the article may be inadequate. Generally therefore it is at least 100,000 and preferably at least 500,000 when the article is an extruded film or fibre but lower values, may be suitable in some shaping process, e.g., for casting or coating. If the molecular weight if too high it may be difficult to shape an adequately concentrated solution of the polymer as a fibre or film. Generally the molecular weight is below 1 million, or at the most 2 million. However where the shaped article can initially be relatively thick, e.g., a coarse film or fibre that may then be stretched if it is desired to reduce its thickness, higher molecular weights, e.g., up to 10 million or more, are sometimes suitable.

The solution that is extruded preferably has a viscosity 20° C. of at least 100,000, and usually at least 120,000 cPs. Often it is in the range 150,000 to 200,000 cPs. Higher values are generally unnecessary. all these viscosities are measured at 20° C. using a Brookfield RVT spindle 7 at 20 rpm. The viscosity desirably is also relatively high at the spinning temperature, which typically is elevated, for instance around 80° C. Preferably therefore the solution at 80° C. has a viscosity of at least 5 or 10,000 cPs and most preferably at least 20,000 cPs. For instance it may be in the range 50,000 to 100,000 cPs. These values may be obtained by extrapolation from values obtained using a Brookfield RVT viscometer spindle 7 at 20 rpm at a range of temperatures somewhat below 80° C.

Shaping of the solution can involve coating the solution on a surface but generally comprises extruding it as a film or fibre. Substantially immediately after extruding or otherwise shaping the solution the linear polymer is caused to form a uniform solid mixture in the form of an article of the desired shape. The article is initially generally very soft. The conversion of the liquid solution to the soft solid articles can be described as precipitation and may involve solvent evaporation, solvent extraction, or other means of insolubilising the polymer.

The shaping can be by wet spinning into an organic solvent that removes water, generally acetone, methylethyl ketone or other lower ketone, or into an inorganic aqueous salt solution such as of lithium chloride or aluminium sulphate. Acetone is preferred.

Alternatively it can be by dry spinning. Preferably it remains slightly damp until the final cross linking in order to maintain softness. In a particularly preferred method, an aqueous solution of the linear polymer is dry spun at a temperature above 150° C., often above 200° C., typically 220° to 270° C. to give a product that is substantially dry on the surface but contains at least 10% residual moisture, the dry spun product is stretched and is cured by heating, generally after collecting the stretched fibre or film.

The internal esterification and cross linking can be promoted by incorporating a catalyst in a solution of the polymer or by exposing the shaped polymer to a catalyst (e.g., by passing the polymer through an atmosphere or solution of a catalyst for the esterification reaction). Generally however the esterification is conducted in the absence of added catalyst. The monomers can be selected such that the esterification is effected by irradiation but generally it is effected by heating the shaped substantially linear polymer to a temperature above 150° C. for sufficient time for the cross linking reaction to occur. For instance it may be 170° C. to 200° C. for 5 to 40 minutes. At higher temperatures shorter reaction times are appropriate, for instance 0.1 to 10 minutes at 200° to 250° C. or up to 300° C. Preferred esterification conditions generally involve heating to 200° to 220° C. for, for instance, 1 to 3 minutes.

Additional components may be included in the solution that is to be shaped in order to modify the properties of the final product. For instance, external plasticiser may be incorporated. The amount of materials other than the cross-linked polymer is generally below 20%, preferably below 10%, by weight of the final article.

The shaped element often has a minor dimension (e.g., the thickness of the film or diameter of fibre) below 1 mm, usually below 500 μm and preferably below 250 μm. However it is usually unnecessary for it to be smaller than 50 μm. The element can have a relatively short major dimension, for instance 1 mm, e.g. in a fibrid, lamella or flake shaped article but generally the final element is a substantially continuous film, a substantially continuous filament, or staple fibre typically having a length of 3 to 100 mm.

The element usually has a gel capacity of at least 50 g deionised water, and at least 20 g 0.9% NaCl aqueous solution, per gram dry polymer.

The element may be provided with additional surface cross-linking, for instance ionic cross-linking with aluminium or other polyvalent metal compound, in order to improve its rate of absorption of liquids.

The resultant absorbent elements may be used in any environment where it is desirable to absorb water, and in particular aqueous electrolyte such as urine or other body fluids, for instance as a replacement for part of the cellulosic fibres in diapers, catamenial appliances, incontinence pads or bandages. When the articles are in the form of fibres they may be scattered into the cellulosic fibres or a film or, preferably, a woven or nonwoven fabric formed of the filaments or fibres may be incorporated in the diaper or other article.

Wound dressing, absorbent wipes and other fabrics may be formed from fibres part or all of which are in accordance with the invention.

Reference should be made to EP 0268498 and EP 0269393 for a general description of suitable plasticising monomers and their amounts, methods of making the linear polymer, suitable molecular weights and concentrations of the resultant aqueous solution of linear monomer, suitable ways of shaping that solution (e.g., by extrusion or impregnation) and of effecting the subsequent cross linking. The entire disclosure of U.S. Ser. No. 123,572 now U.S. Pat. No. 4,962,172 filed 20th Nov. 1987 by A. Allen, D. Farrar and P. Flesher is hereby incorporated by reference.

The following are examples.

EXAMPLE 1

Three copolymer solutions in water were prepared (1, 2 and 3) from monomers containing 1, 2 and 3% by weight respectively of hexapropylene glycol monomethacrylate. The rest of each copolymer comprised 20% by weight of methyl acrylate and the balance was 75 mole % neutralised sodium acrylate/acrylic acid. The polymer concentrations of the solutions (as weight %) and solution viscosity (Brookfield RVT at 20 rpm spindle 7 at 20° C. - in cp) for polymers 1, 2 and 3 were respectively 3.6 and 214,000, 32.3 and 136,000 and 35.3 and 162,000. Approximately 100 micron thick films of these polymers were prepared and heated for various times at 220° C. to effect cross linking. The free swell, retention and % by weight soluble polymer in 0.9% sodium chloride solution for each heat treated film were determined and are given in the following table:

| Time at 220° C. (minutes) | Polymer 1 | | | Polymer 2 | | | Polymer 3 | | |
|---|---|---|---|---|---|---|---|---|---|
| | FS | RET | PSP | FS | RET | PSP | FS | RET | PSP |
| 0.5 | | | | | | | 16 | 15 | 80 |
| 1 | | | | | | | 24 | 23 | 80 |
| 2 | | | | 16 | 13 | 50 | 34 | 33 | 42 |
| 4 | | | | | | | 53 | 52 | 25 |
| 5 | 32 | 30 | 49 | 55 | 52 | 35 | 59 | 57 | 21 |
| 7.5 | | | | 61 | 56 | 24 | | | |
| 10 | 46 | 43 | 19 | 44 | 39 | 19 | 42 | 35 | 16 |
| 12 | | | | | | | 34 | 23 | 12 |
| 15 | 55 | 50 | 16 | 32 | 24 | 12 | | | |
| 20 | 51 | 44 | 12 | | | | | | |
| 25 | 38 | 24 | 7 | | | | | | |

FS = Free swell (gm/gm)
RET = Retention (gm/gm)
PSP = Percentage soluble polymer (% w/w)

EXAMPLE 2

Three copolymers were prepared (1, 2 and 3) from monomers containing 1, 2 and 3% by weight respectively of hexapropylene glycol monomethacrylate. The rest of the copolymer comprised 20% by weight of methyl acrylate and the balance was 75 mole % neutralised sodium acrylate/acrylic acid.

Three further copolymers 4, 5 and 6 were produced in the same way from monomers containing 1, 2 and 3% respectively of hydroxy propylmethacrylate with the same amounts of methyl acrylate, sodium acrylate and acrylic acid as before.

All the polymer solutions were prepared to give a similar molecular weight and distribution at a concentration of 33.0% by weight and viscosities between 1000 and 1200 poise.

Approximately 100 micron thick films of these polymers were prepared and heated for varous times ranging from 1 minute up to 25 minutes at 220° C. to effect cross linking. In each instance the time was selected by experiment to give the maximum free swell value.

The free swell, retention and % by weight of soluble polymer in 0.9% sodium chloride solution for each heat treated film were determined. From this data are summarised the figures in the table below. These results clearly show that polymer prepared using hexapropylene glycol monomethacrylate achieve a higher capacity for adsorption than polymers prepared using hydroxypropyl methacrylate.

| Polymer | Free Swell (gm/gm) | Retention (gm/gm) | Time @ 220° C. (mins) |
|---|---|---|---|
| 1 | 55 | 50 | 15 |
| 2 | 62 | 59 | 7 |
| 3 | 62 | 59 | 6 |
| 4 | 43 | 36 | 14 |
| 5 | 48 | 40 | 8 |
| 6 | 48 | 46 | 5 |

I claim:

1. A water absorbent, water insoluble, polymeric element having a gel capacity of at least 50 grams deionised water per gram dry polymer and that has been made by a process comprising providing a solution of a water soluble, substantially linear, polymer that has been made by copolymerisation of a water soluble blend of monoethylenically unsaturated monomers comprising at least 50% by weight carboxylic monomer that provides carboxyl groups and 0.1 to 15% by weight hydroxylic monomer that provides hydroxyl groups and that has the formula $CHR^1=CR^2-Y-M_1-H$ where $R^1$ is hydrogen or carboxy, $R^2$ is hydrogen, carboxy or methyl, Y is O, $CH_2O$ or COO, M is alkyleneoxy and a is at least 5, shaping the solution by a shaping step selected from extrusion, coating, impregnation and foaming to shape the linear polymer into the shape of the desired element, and then heating the shaped element to cause the said carboxylic and hydroxylic groups to react in the shaped element to form cross linkages of the formula $-Y-M_a-OCO-$ where Y, M and a are as defined above.

2. An element according to claim 1 in which the monomer blend contains 10 to 45% by weight plasticising monomer selected from alkyl esters of ethylenically unsaturated acids, acrylonitriles, styrenes, and vinyl esters.

3. An element according to claim 1 in which $R^1$ is hydrogen, $R^2$ is hydrogen or methyl, M is selected from ethyleneoxy, propyleneoxy and butyleneoxy, Y is COO and a is from 5–100.

4. An element according to claim 3 in which the blend comprises 0.1 to 10% by weight of the hydroxylic monomer, 50 to 89.9% by weight acrylic acid (or water soluble salt thereof) and 10 to 30% by weight methyl acrylate.

5. An element according to claim 1 in which $M_a$ is hexapropyleneoxy.

6. An element according to claim 1 in which the shaping is by extrusion of the solution as a fibre or film and substantially immediately precipitating the polymer in the extruded fibre or film.

7. An element according to claim 6 in which the fibre or film is stretched before the formation of the cross linkages.

8. An element according to claim 1 in which the blend is wholly free of di- and poly- ethylenically unsaturated monomer.

9. An element according to claim 4 in which $R^2$ is methyl and $M_a$ is hexapropyleneoxy.

10. An element according to claim 1 in which a is 6 to 20.

11. An element according to claim 3 in which a is 6 to 10.

12. In a water absorbent, water insoluble, polymeric element having a gel capacity of at least 50 grams deionized water per gram dry polymer and that has been made by a process comprising providing a solution of a water soluble, substantially linear, polymer that has been made by copolymerization of a water soluble blend of monoethylenically unsaturated monomers comprising at least 50% by weight carboxylic monomer that provides carboxyl groups and 0.1 to 15% by weight hydroxylic monomer that provides hydroxyl groups and that has the formula $CHR^1=CR^2-Y-M_a-H$ where $R^1$ is hydrogen or carboxy, $R^2$ is hydrogen, carboxy or methyl, Y is O, $CH_2O$ or COO, and M is alkyleneoxy, shaping the solution by a shaping step selected from extrusion, coating, impregnation and foaming to shape the linear polymer into the shape of the desired element, and then heating the shaped element to cause the said carboxylic and hydroxylic groups to react in the shaped element to form cross linkages of the formula $-Y-M-OCO-$ where Y, M and a are as defined above, the improvement which comprises a being at least 5.

13. An element according to claim 12 in which a is 6 to 20.

14. An element according to claim 13 in which a is 6 to 10.

* * * * *